United States Patent [19]

Schneider

[11] Patent Number: 5,654,510

[45] Date of Patent: Aug. 5, 1997

[54] ULTRASONIC TRANSDUCER APPARATUS FOR TESTING RAILROAD WHEELS

[75] Inventor: Friedhelm Schneider, Wegberg, Germany

[73] Assignee: Hegenscheidt-MFD GmbH, Erkelenz, Germany

[21] Appl. No.: 535,557

[22] Filed: Sep. 28, 1995

[30] Foreign Application Priority Data

Oct. 1, 1994 [DE] Germany ............... 9415885 U

[51] Int. Cl.$^6$ ............... G01N 29/04
[52] U.S. Cl. ............... 73/622; 73/602
[58] Field of Search ............... 73/1 DV, 598, 73/629, 622, 637, 638, 600, 602; 364/508, 507

[56] References Cited

U.S. PATENT DOCUMENTS

| | | |
|---|---|---|
| 4,435,984 | 3/1984 | Gruber ............... 73/1 DV |
| 4,651,568 | 3/1987 | Reich ............... 73/622 |
| 5,113,697 | 5/1992 | Schlawne ............... 73/622 |

*Primary Examiner*—Christine K. Oda
*Attorney, Agent, or Firm*—W. G. Fasse; W. F. Fasse

[57] ABSTRACT

An ultrasonic transducer apparatus includes an emitter for emitting pulsed ultrasonic signals into a railroad wheel to be tested and at least one receiver for receiving the corresponding echo signals from the wheel. Transmission of the ultrasonic signals into the wheel as well as the return transmission of signals from the wheel to the receiver can be carried out in a contacting and/or non-contacting manner. The emitter (2) and the receiver (3) are arranged spaced apart from one another around the circumference of the railroad wheel (1), with a sufficient spacing distance that the receiver (3) is arranged outside of a symmetrical range (4) about the centerline (6) of the emitter (2) in which superposition of the two pulse packets of ultrasonic signals travelling around the wheel can arise.

15 Claims, 1 Drawing Sheet

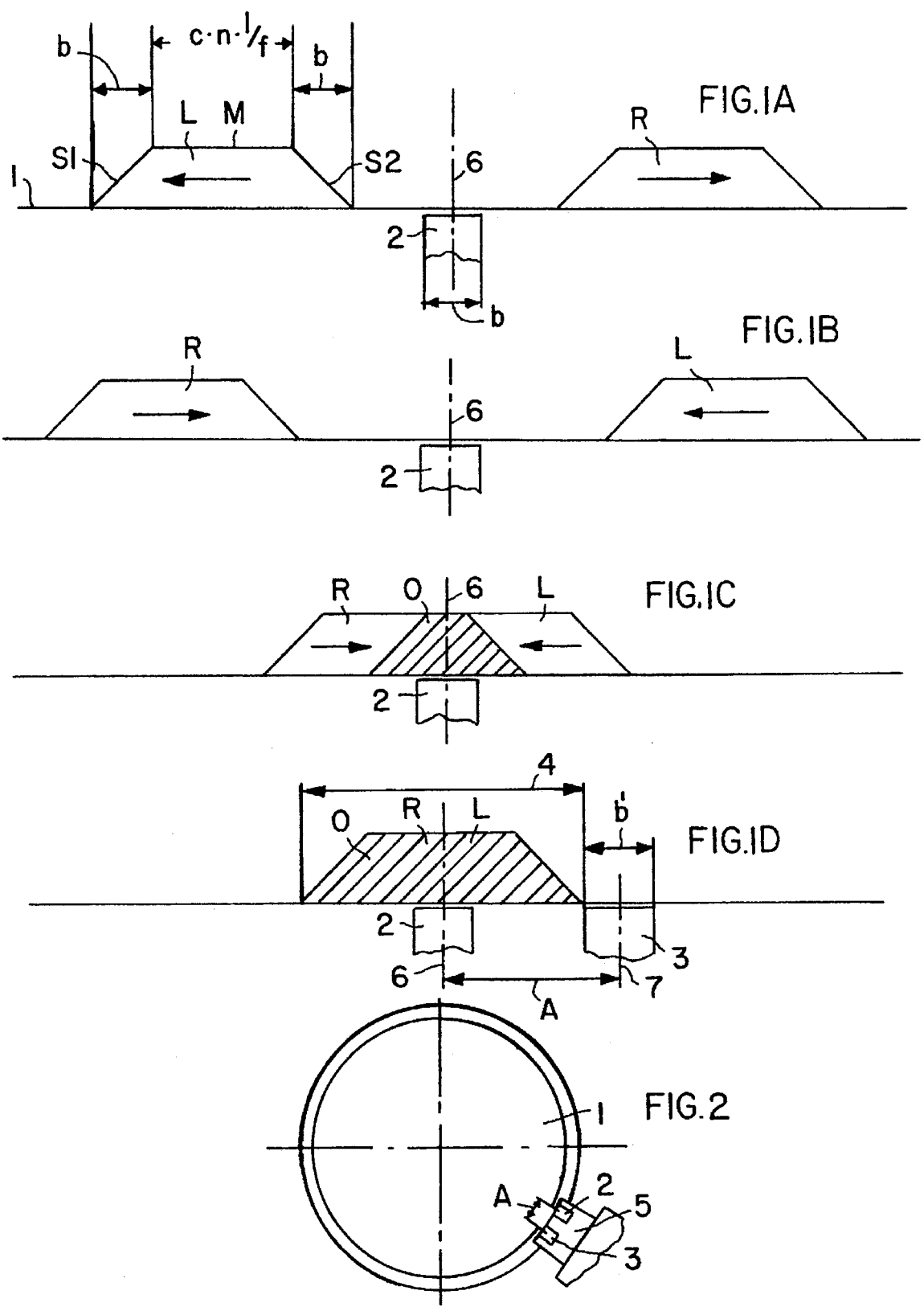

ULTRASONIC TRANSDUCER APPARATUS FOR TESTING RAILROAD WHEELS

FIELD OF THE INVENTION

The invention relates to an ultrasonic transducer arrangement for testing railroad wheels to detect cracks and the like, including at least one transmitter or emitter for emitting pulsed ultrasonic signals and at least one receiver for receiving the corresponding echo signals. The transmission of the ultrasonic signals into the railroad wheel to be tested as well as the retransmission of the signals from the railroad wheel back to the receiver is carried out in a non-contacting and/or a contacting manner.

BACKGROUND INFORMATION

Ultrasonic transducer arrangements of the above described type are generally known and are used for economically testing railroad wheels while the wheels are in their normal installed state. A train simply drives slowly over a test path that is provided with such ultrasonic transducers. One type of known ultrasonic transducer arrangement produces the ultrasonic signals by means of piezo-elements and then transmits the ultrasonic signals into the wheel set through a coupling fluid contained in a bladder. A grave disadvantage of such systems is that the bladder containing the coupling fluid often ruptures or leaks.

In addition to the above described ultrasonic transducer systems using a coupling fluid, other ultrasonic transducers are known, whereby the ultrasonic oscillations or vibrations are transmitted into the railroad wheel in a non-contacting manner. Such known ultrasonic transducers are generally based on an electrodynamic method, wherein the production of the ultrasonic pulse in the railroad wheel always produces two pulse packets or groups of pulses, which are each a segment of a wave train, that travel in opposite directions around the wheel. Both pulse packets will require the same amount of time to travel once around the wheel, because both pulses will travel the exact same path distance corresponding to the length of the circumference of the wheel. Thus, the two pulse packets, namely the right-travelling and the left-travelling pulse packets, will meet each other or coincide back at the same point at which the ultrasonic waves were produced. In other words, one pulse packet will travel clockwise around the wheel, and one pulse packet will travel counterclockwise around the wheel, but the two pulse packets will both get back to the same starting point at exactly the same moment.

In the second type of ultrasonic transducer arrangements described above, the ultrasonic pulses are produced by means of an emitter that is arranged in a testing head, and the corresponding echo signals are received by means of a receiver that is arranged immediately adjacent or even integrated into the emitter unit in the testing head. Because the two pulse packets travel around the railroad wheel in opposite directions and arrive back at the starting point together after having travelled once around the wheel, as described above, at that time they will become superimposed on one another in an area or range around the location of pulse generation, i.e. the area of the emitter unit. Depending upon the relation between the circumference of the wheel and the wavelength of the ultrasonic vibrations introduced into the wheel, the superposition of the two pulse packets will have a different characteristic. For example, the two pulse packets may be superimposed peak-on-peak, to result in a doubling of the total amplitude. On the other hand, it could occur that the two pulse packets are superimposed peak-on-trough, whereby the over-lapped or superimposed pulse packets locally cancel each other out to a zero amplitude. It is also possible that any intermediate form between a peak-to-peak or peak-to-trough superposition can occur.

The above superposition thus causes the grave disadvantage that the receiver will receive the return or turn-around signal with different signal strengths, depending on the diameter of the wheel and the wave-length of the ultrasonic vibrations. Since the amplitude of the received echo or turn-around signal is used as the reference magnitude for determining whether other signals indicate that cracks are present in the wheel, the evaluation of the turn-around signal will involve great uncertainties. These other signals are generally called error signals. As a result of the above problems, the examination of wheel sets for cracks or the like using ultrasonic transducers according to the prior art often gives erroneous results. As a consequence of such erroneous testing results, unnecessary high costs will be suffered when a wheel set that is actually defect-free is removed from a train. On the other hand, the danger exists that undetected cracks in a wheel set will result in serious operation interruptions or even breakdowns and accidents during the operation of the railroad vehicle.

OBJECTS OF THE INVENTION

In view of the above it is the aim of the invention to achieve the following objects singly or in combination:
- to improve an ultrasonic transducer arrangement in such a manner that the detection of cracks and the like is improved and the diagnosis regarding the quality of a wheel or the like can be made with greater certainty;
- to avoid the reception of superimposed turn-around signals resulting from a superposition of two pulse packets that have travelled around a wheel in opposite directions;
- to exclude the wheel diameter as a factor to be considered in evaluating echo signals received by the receiver unit;
- to arrange an ultrasonic transducer and an ultrasonic receiver at a defined minimum spacing from one another sufficient to avoid the reception of superimposed turn-around signals, so as to achieve the above listed objects while also providing a compact ultrasonic testing head; and
- to provide such a compact ultrasonic testing head that can operate in a contacting or non-contacting manner with the wheel as desired, to be easily applicable to a broad variety of different wheels, while avoiding the use of coupling fluids and the like as desired.

SUMMARY OF THE INVENTION

The above objects have been achieved in an ultrasonic transducer apparatus according to the invention, wherein an emitter and a receiver are arranged sufficiently far apart around the circumference of a railroad wheel, so that the receiver is located outside of a symmetrical range about the centerline of the emitter in which two pulse packets of ultrasonic signals travelling around the wheel in opposite directions will be superimposed after travelling one circuit around the wheel.

According to the invention, it is achieved that the receiver does not fall within the region of superposition of the left-travelling and the right-travelling pulse, and thereby the undesirable reception of interference signals in the form of superimposed pulse packets is avoided. As a result, the receiver first receives the pulse packet travelling in one direction, and then receives the pulse packet travelling in the opposite direction, in time-staggered succession. Thus, the form and amplitude of the received trun-around signal is no longer related to the diameter of the railroad wheel, and can therefore be used as a reliable reference for estimation of the cracks indicated by the error signals in the wheel set that has been tested. According to the invention, interference resulting from the superposition of two pulse packets cannot have any effect on the reliability of the analysis.

A particularly advantageous embodiment of the invention specifies that the spacing distance A between the centerline of the emitter and the centerline of the receiver should be defined at least approximately as $$A = b + \tfrac{1}{2}(c \cdot n \cdot 1/f) + \tfrac{1}{2}b'$$

wherein:
A: is the spacing distance between the centerline of the emitter and the centerline of the receiver;
b: is the width of the emitter;
b': is the width of the receiver;
c: is the velocity of sound in the railroad wheel;
n: is the number of vibrations per pulse packet; and
f: is the frequency of the ultrasonic vibrations.

When the spacing A is set as specified above, the receiver will be arranged in the closest possible position relative to the emitter so as to just avoid the reception of any turn-around signal that arises from the superposition of the left-travelling and the right-travelling ultrasonic pulses. Minimizing the spacing distance in this manner is very advantageous, because the region of the wheel in which it is impossible to detect any cracks that may exist can thereby be limited to a very small length. A further advantage of minimizing the spacing between the emitter and the receiver in the above described manner is that the structural space required for the ultrasonic transducer can be kept quite small.

A further feature of the invention provides that the emitter and the receiving coil can both be arranged in a single common testing head. In this manner it is ensured that the emitter and the receiver constantly have the same fixed spacing from one another, whereby it is guaranteed that superpositions of the right-travelling and left-travelling pulse packets will not affect the received turn-around signals. Furthermore, the common arrangement of both coils in one testing head greatly simplifies the possibility of synchronously moving and applying both coils to the railroad wheel to be tested, and the set-up time for carrying out a testing procedure is considerably reduced.

BRIEF DESCRIPTION OF THE DRAWINGS

In order that the invention may be clearly understood, it will now be described, by way of example, with reference to the accompanying drawings, wherein:

FIGS. 1A to 1D show successive schematic representations of a cylindrical projection of the running surface of a wheel being tested, graphically showing two pulse packets emitted by an emitter and travelling around the wheel in opposite directions to be received by the receiver; and FIG. 2 is a schematic view of a testing head incorporating an emitter and a receiver and being arranged in contact with a railroad wheel.

DETAILED DESCRIPTION OF PREFERRED EXAMPLE EMBODIMENTS AND OF THE BEST MODE OF THE INVENTION

FIG. 1A shows an ultrasonic emitter 2 having a width b and a centerline 6, that has emitted two pulse packets L and R that travel around the circumference of a railroad wheel 1 in opposite directions. More specifically, the pulse packet L travels toward the left, or clockwise around the wheel 1, and the pulse packet R travels to the right or counterclockwise around the wheel 1. For the sake of clarity in the graphical representation of FIGS. 1A to 1D, the circumference of the wheel 1 is represented by its cylindrical projection onto a straight line. The height of each of the pulse packets along the circumference of the wheel 1 represents the energy of the pulse packet. Because the two pulse packets L and R were generated at the same time and have the same velocity, namely the velocity of sound c in the railroad wheel, the two pulse packets L and R will always be spaced the same distance away from the centerline 6 of the emitter 2.

The size and form of each pulse packet L and R is defined as follows. The ultrasonic pulse packets L and R are generated over the width b of the emitter 2, whereby the energy of the pulse increases over this distance b from zero to its final maximum value, which thereby generates a shoulder region S1 of width b. Then, the energy remains constant at its maximum level in a region M over a distance $c \cdot n \cdot 1/f$, whereby f is the frequency of the sound vibrations in the railroad wheel, and n is the number of vibrations or oscillations in one pulse packet, which in turn is dependent upon the time duration of ultrasonic emission. After the segment M having a constant energy, a second shoulder region S2 follows, in which the energy level drops down to zero again over a length b. Both of the pulse packets L and R may have identical packet energy distribution shapes.

FIG. 1B is a graphical image similar to that of FIG. 1A, but shows a later time-step, when the two pulse packets have travelled substantially around the circumference of the wheel 1 and are now approaching each other from opposite sides near the emitter 2. At a time between that shown in FIG. 1A and that shown in FIG. 1B, the two pulse packets L and R approached each other and then overlapped and crossed at a point on the wheel exactly diametrically opposite the emitter 2. Just as explained above regarding FIG. 1A, the spacing or distance between each of the impulse packets R and L and the center line 6 of the emitter 2 is the same, since both pulse packets have covered the same distance due to their identical velocities.

FIG. 1C shows a situation resulting a short time after that of FIG. 1B. In FIG. 1C, the two pulse packets R and L have continued to approach each other, and have already become partly overlapped or superimposed in the shaded region O. The shaded superimposed region O is symmetrical about the centerline 6 of the emitter 2.

FIG. 1D shows the situation arising a short time after that shown in FIG. 1C, namely wherein the two pulse packets R and L are exactly superimposed on one another, as was also the case at the time the two pulse packets R and L were generated. The length of the range 4, i.e. the maximum extent or range in which the two oppositely-travelling pulse packets are superimposed on one another, corresponds to the total width of one pulse packet. Thus, the size of range 4 is given by the sum of twice the emitter width b and the length $c \cdot n \cdot 1/f$ of the range M in which the energy of the pulse packet was held constant. The range 4 is symmetrical about the centerline 6 of the emitter 2. Outside of the range 4, no superposition or overlapping of the oppositely travelling packets R and L will arise. Thus, the point farthest away from the centerline 6 of the emitter 2 at which a superposition of signals can still arise will be spaced a maximum distance of $b + \tfrac{1}{2}(c \cdot n \cdot 1/f)$, respectively in both directions from the centerline 6. In other words, outside of the range 4, the two pulse packets R and L will pass any particular point in time-staggered succession which allows a time-separated evaluation of the two echo signals. It should be understood, that a similar overlapping or superimposed zone exists on the diametrically opposite side of the wheel, so that the separated evaluation of the two signals would not be possible either at such a diametrically opposite range.

FIG. 1D further shows a receiver 3 having the width b' arranged according to the invention. The centerline 7 of this receiver 3 is located a spacing distance A away from the centerline 6 of the emitter 2, whereby the minimum spacing distance A is defined approximately as: $a=b+\frac{1}{2}(c \cdot n \cdot 1/f)+\frac{1}{2}b'$. This spacing distance A is the minimum distance between the two centerlines 7 and 6, whereby the receiver 3, having a total width b', is arranged just far enough from the emitter 2 so that no part of the receiver 3 falls into the range 4 where superposition of the opposite pulse packets R and L can occur. Minimizing this spacing distance A according to the just stated formula is advantageous, because then the structural space required for the ultrasonic transducer is held to its absolute minimum.

FIG. 2 shows a testing head 5 in which both the emitter 2 and the receiver 3 are arranged. The testing head 5 is arranged on the running surface of a railroad wheel 1 that is to be tested for cracks. With a minimized spacing distance A between the emitter 2 and the receiver 3, the overall dimensions of the testing head 5 can be made relatively small, whereby its ease of use is improved, and accessibility to the railroad wheel in confined spaces is also improved. By arranging the emitter 2 and the receiver 3 at a constant fixed spacing distance from each other in a testing head 5, whereby the spacing distance is specified depending upon the testing frequency to be used, it becomes unnecessary to perform adjustments of the two coils relative to each other, and the set-up time necessary for carrying out a test is minimized. Furthermore, the emitter and receiver can be arranged in the testing head 5 with an adjustable spacing between them, to allow the spacing distance to be selected corresponding to a particular testing frequency to be used. The testing head 5 is arranged in a contacting or non-contacting manner relative to the wheel 1 for carrying out a test, as will be understood by persons skilled in the present art. The present apparatus can be used as well for testing various articles other than railroad wheels.

Although the invention has been described with reference to specific example embodiments, it will be appreciated that it is intended to cover all modifications and equivalents within the scope of the appended claims.

What is claimed is:

1. An ultrasonic transducer apparatus for testing an article to detect the presence of defects therein, said apparatus comprising an emitter of pulsed ultrasonic signals adapted to introduce said signals into said article as first and second pulse packets travelling in opposite directions around a circumference of said article, and a receiver adapted to receive ultrasonic echo signals from said article, wherein said emitter and said receiver are spaced apart from each other at a sufficient spacing distance (A) so that said receiver is located outside a symmetrical range, extending along said circumference and centered on a centerline of said emitter, in which said first and second pulse packets are superimposed on each other.

2. The apparatus of claim 1, wherein said emitter contacts said article to introduce said signals into said article.

3. The apparatus of claim 1, wherein said emitter does not directly contact said article to introduce said signals into said article.

4. The apparatus of claim 1, wherein said spacing distance (A) is measured between said centerline of said emitter and a centerline of said receiver, and said spacing distance (A) is at least about $$b+\tfrac{1}{2}(c \cdot n \cdot 1/f)+\tfrac{1}{2}b',$$

wherein b is the width of said emitter, b' is the width of said receiver, c is the velocity of sound in said article, n is the number of oscillations in each of said pulse packets, and f is the frequency of said ultrasonic signals.

5. The apparatus of claim 4, wherein said spacing distance (A) is equal to about $b+\tfrac{1}{2}(c \cdot n \cdot 1/f)+\tfrac{1}{2}b'$.

6. The apparatus of claim 5, further comprising a common testing head, in which both said emitter and said receiver are arranged.

7. The apparatus of claim 1, further comprising a common testing head, in which both said emitter and said receiver are arranged.

8. The apparatus of claim 1, wherein said spacing distance A is further limited so that said receiver is located outside a second symmetrical range, centered diametrically opposite said emitter on said circumference of said article, in which said first and second pulse packets are superimposed on each other.

9. A method of testing an article to detect the presence of defects therein, said method comprising:
   a) arranging an ultrasonic emitter centered at a first local along a circumference of said article;
   b) arranging an ultrasonic receiver centered at a second local along said circumference of said article;
   c) emitting pulsed ultrasonic signals from said emitter into said article as first and second pulse packets that travel in opposite directions around said circumference and become superimposed on each other at a symmetrical range centered at said first location; and
   d) receiving said first and second pulse packets with said receiver;

wherein said first location and said second location are spaced apart a sufficient spacing distance (A) so that said receiver is located outside of said symmetrical range in which said pulse packets are superimposed.

10. The method of claim 9, wherein said step d) comprises receiving said first and second pulse packets in time succession.

11. The method of claim 9, wherein said steps a) and b) are carried out so that said spacing distance (A) is at least about $$b+\tfrac{1}{2}(c \cdot n \cdot 1/f)+b',$$

wherein b is the width of said emitter, b' is the width of said receiver, c is the velocity of sound in said article, n is the number of oscillations in each of said pulse packets, and f is the frequency of said ultrasonic signals.

12. The method of claim 11, wherein said spacing distance (A) is equal to about $b+(c \cdot n \cdot 1/f)+\tfrac{1}{2}b'$.

13. The method of claim 9, wherein said spacing distance (A) is further limited so that said receiver is arranged outside of a second symmetrical range, centered diametrically opposite said first location, in which said first and second pulse packets are superimposed on each other.

14. The method of claim 9, wherein said step a) comprises arranging said emitter in contact with said article.

15. The method of claim 9, wherein said step a) comprises arranging said emitter out of direct contact with said article.

* * * * *

UNITED STATES PATENT AND TRADEMARK OFFICE
CERTIFICATE OF CORRECTION

PATENT NO. : 5,654,510
DATED : August 5, 1997
INVENTOR(S) : Schneider It is certified that error appears in the above-identified patent and that said Letters Patent is hereby corrected as shown below.

On the Title page, in the References Cited, replace
"4,651,568 3/1987 Reich" by
--4,651,568 3/1987 Reich et al.--;

| | | |
|---|---|---|
| Col. 3 | line 3 | replace "trun-around" by --turn-around--; |
| Col. 4 | line 58 | replace "energy-of" by --energy of--; |
| Col. 6 | line 27 | replace "local" by --location--; |
| | line 31 | replace "local" by --location--; |
| | line 56 | replace "b+· " by --b+½--. |

Signed and Sealed this

Twenty-first Day of October 1997

*Attest:*

BRUCE LEHMAN

*Attesting Officer*     *Commissioner of Patents and Trademarks*